United States Patent [19]

Cain et al.

[11] 4,338,326

[45] Jul. 6, 1982

[54] PHENOXYPYRIDINEMETHYL ESTERS OF 4-ALKENOIC ACIDS

[75] Inventors: Paul A. Cain, Dunbar; Thomas N. Wheeler, Charleston, both of W. Va.

[73] Assignee: Union Carbide Corporation, Danbury, Conn.

[21] Appl. No.: 97,782

[22] Filed: Nov. 27, 1979

[51] Int. Cl.$^3$ .................. A01N 43/40; C07D 213/55; C07D 213/57

[52] U.S. Cl. .................... 424/267; 546/268; 546/261; 546/300; 546/302; 71/94

[58] Field of Search ............... 546/268, 300, 261, 302; 424/263; 71/94

[56] References Cited

U.S. PATENT DOCUMENTS

| | | | |
|---|---|---|---|
| 2,228,172 | 10/1980 | Malhotra et al. | 424/263 |
| 4,039,680 | 8/1977 | Fujimoto et al. | 424/275 |
| 4,042,710 | 8/1977 | Bull et al. | 424/304 |
| 4,058,622 | 11/1977 | Fujimoto et al. | 424/308 |
| 4,062,968 | 12/1977 | Fujimoto et al. | 424/275 |
| 4,163,787 | 8/1979 | Malhotra et al. | 424/263 |
| 4,221,799 | 9/1980 | Van Heertum et al. | 546/300 |
| 4,223,033 | 9/1980 | Henrick | 546/300 |
| 4,224,330 | 9/1980 | Henrick et al. | 424/263 |
| 4,226,872 | 10/1980 | Henrick et al. | 424/263 |

FOREIGN PATENT DOCUMENTS

| | | | |
|---|---|---|---|
| 862499 | 6/1978 | Belgium | 424/ |
| 860687 | 5/1978 | Belgium | 424/ |
| 2810881 | 9/1978 | Fed. Rep. of Germany | 424/ |

OTHER PUBLICATIONS

Morrison & Boyd, "Organic Chemistry", Third Edition, pp. 602–603, (Allyn & Bacon) (1973).

*Primary Examiner*—Robert T. Bond
*Attorney, Agent, or Firm*—John A. Shedden; Gerald L. Coon

[57] ABSTRACT

Novel phenoxypyridinemethyl esters of 4-alkenoic acid compounds having pesticidal activity and methods of their preparation.

12 Claims, No Drawings

PHENOXYPYRIDINEMETHYL ESTERS OF 4-ALKENOIC ACIDS

BACKGROUND OF THE INVENTION

1. Field of the Invention

This invention relates to novel phenoxypyridinemethyl esters of 4-alkenoic acid compounds having pesticidal activity and methods of their preparation.

2. Description of the Prior Art

Esters of isovaleric acid are disclosed in U.S. Pat. No. 4,042,710, including 2-substituted isovalerates having the structural formula I:

$$\underset{R-CH-C-O-CH-Y}{\overset{H_3C\diagdown\diagup CH_3\quad O\quad X}{\phantom{X}\phantom{X}\phantom{X}\phantom{X}\phantom{X}\phantom{X}\overset{\|}{\phantom{X}}\phantom{X}\phantom{X}}} \quad \text{I}$$

in which R represents an alkyl group of 1 to 16 carbon atoms (which may be branched), an alkenyl group of up to 6 carbon atoms, or a benzyl group optionally substituted by one or more halogen atoms.

U.S. Pat. Nos. 4,039,680; 4,062,968; and 4,058,622 all disclose esters having the general structure II:

$$\underset{R_9}{\overset{R_8}{\diagdown}}C=C\underset{\underset{CH-C-O-CH-Y}{\overset{Z\quad O\quad X}{|\quad \|\quad |}}}{\overset{R_7}{\diagup}} \quad \text{II}$$

where $R_7$ may be H, $CH_3$, or $CH_2CH_3$; $R_8$ is H or $CH_3$; $R_9$ is $CH_3$; Z is an alkyl group having from 1 to 3 carbon atoms.

Belgium Pat. No. 862,499 discloses a group of pyrethroidal esters which are characterized by the so-called "Pydrin alcohol" and a class of olefinic esters. The pesticidal phenoxy benzyl pentene carboxylates are prepared by esterifying a phenoxy benzyl alcohol with pentene carboxylic acid. According to the disclosure of Belgium Pat. No. 862,499, esters are prepared using a synthetic method from acids of the general formula III:

$$\underset{R_7}{\overset{R_6}{\diagdown}}C=C\underset{\underset{R_2}{\diagup}\overset{|}{C}\underset{R_5}{\diagdown}}{\overset{H\quad R_4}{\diagup}\overset{|}{\underset{I}{CH-CO_2H}}} \quad \text{III}$$

wherein
$R_4$ = lower alkyl
$R_2$ and $R_5$ = H or an alkyl group having from 1–4 carbon atoms $R_6$ and $R_7$ = Cl or Br Belgium Pat. No. 860,687 discloses phenoxybenzyl haloalkenoate esters which are useful as insecticides and acaricides and have the following structural formula IV:

$$\underset{Y}{\overset{X}{\diagdown}}C=C\underset{CH_2CHCO_2CH}{\overset{H\quad CH_3\quad R_1}{\diagup\phantom{X}\phantom{X}\overset{|}{\phantom{X}}\phantom{X}\phantom{X}\overset{|}{Z}}}\text{—}\bigcirc\text{—O—}\bigcirc \quad \text{IV}$$

wherein X is halogen, Y is halogen or $CH_3$, Z is CN or ethynyl, and $R_1$ is H or $CH_3$.

German Offenlegungsschrift No. 2,810,881 discloses insecticidal phenoxy- or phenylthio-pyridyl methyl ester derivatives prepared from 3,3-dichlorovinyl-2,2-dimethylcyclopropanecarboxylic acid. The cyclopropanecarboxylic acid pyridylmethyl ester derivatives disclosed therein have the following structural formula V:

$$(X)_n\text{—}\bigcirc\text{—}\underset{H}{\overset{}{Y}}\text{—}\bigcirc\underset{N}{\overset{}{}}\text{—}\underset{R}{\overset{}{CHCOC}}\overset{O}{\overset{\|}{C}}\underset{\diagdown CH=C(Z)_2}{\overset{\diagup CH_3}{\overset{-CH_3}{}}} \quad \text{V}$$

wherein:
X is an alkyl group having from 1–4 carbon atoms, an alkoxy group having from 1–4 carbon atoms, an alkylthio group having from 1–4 carbon atoms, an alkylsulphonyl group having from 1–4 carbon atoms, $CF_3$, 3,4-methylenedioxy, Cl, F or Br;
n is 0, 1 or 2;
Y is O or S;
R is H, CN or ethynyl; and
Z is Cl, F or Br.

BRIEF DESCRIPTION OF THE INVENTION

This invention relates to compounds corresponding to the following general formula VI:

$$\underset{R_2}{\overset{R_1}{\diagdown}}C=C\underset{\underset{R_4}{\diagup}\overset{|}{C}\underset{R_5}{\diagdown}}{\overset{R_3}{\diagup}\overset{R_6}{\underset{|}{\overset{}{C}}}\underset{}{\overset{O}{\underset{\|}{C}}}\overset{X}{\underset{|}{\overset{}{C}}}\text{—CH—}\bigcirc\underset{N\quad R_9}{\overset{R_7\quad R_8}{}}\text{—O—}\bigcirc\underset{R_{14}}{\overset{R_{11}\quad R_{12}}{\underset{R_{13}}{}}}} \quad \text{VI}$$

wherein:
$R_1$, $R_2$, and $R_3$ may be independently hydrogen, a lower alkyl group having from 1 to 3 carbon atoms or halogen;
$R_4$ and $R_5$ may be independently hydrogen, a lower alkyl group having from 1 to 5 carbon atoms, polyhaloalkyl, haloalkyl, halogen, a lower alkenyl group having from 2 to 5 carbon atoms, a lower cycloalkyl group having from 3 to 5 carbon atoms, a lower cycloalkenyl group having from 3 to 5 carbon atoms, cyano, nitro, a lower alkoxy group having from 1 to 3 carbon atoms, aryloxy, a lower alkylthio group having from 1 to 3 carbom atoms, arylthio, a lower alkylsulfonyl group having from 1 to 3 carbon atoms, alkylsulfinyl, arylsulfonyl, arylsulfinyl, acylamido, or a lower dialkylamino group having from 1 to 3 carbon atoms;

R$_6$ may be an alkyl group having from 1 to 5 carbon atoms, branched alkyl, cycloalkyl, alkenyl, branched alkenyl, or cycloalkenyl;

X may be hydrogen, cyano, ethynyl, thioamido, alkyl, cyckoalkyl, alkenyl, polyhaloalkenyl, or dihaloallyl with no more than seven carbon atoms in any one aliphatic group.

R$_7$, R$_8$, and R$_9$ may be individually hydrogen, halogen, nitro, cyano, cycloalkyl, polyhaloalkyl, alkyl, alkoxy, alkenyl, polyhaloalkenyl, cycloalkenyl, phenyl, phenoxy, alkylthio, phenylthio, alkylsulfinyl, phenylsulfinyl, alkylsulfonyl, phenylsulfonyl, acylamino or dialkylamino with no more than seven carbon atoms in any one aliphatic group and two adjacent substituents may be joined by an alkylene, polyhaloalkylene, alkenylene, or polyhaloalkenylene groups to form a 5, 6, or 7-membered ring or by a carbon chain completing a benzene ring fused to the pyridine nucleus;

R$_{10}$, R$_{11}$, R$_{12}$, R$_{13}$, and R$_{14}$ may individually be halogen, nitro, cyano, hydrogen, alkyl, cycloalkyl, polyhaloalkyl, phenyl phenoxy, alkoxy, alkenyl, polyhaloalkenyl, cycloalkenyl, phenylthio, alkylthio, phenylsulfinyl, alkylsulfonyl, phenylsulfonyl, acylamino or dialkylamino with no more than seven carbon atoms in any one aliphatic group and any two adjacent substituents may also be joined by an alkylene, polyhaloalkylene, alkenylene, polyhaloalkenylene group completing a 5-, 6-, or 7-membered ring or by a carbon chain completing a benzene ring fused to the phenoxy nucleus.

Structure VI is understood to include geometrical isomers about the C$_4$-C$_5$ bond and optical isomers at C$_2$. Preferred compounds according to this invention are those having the following general formula VII:

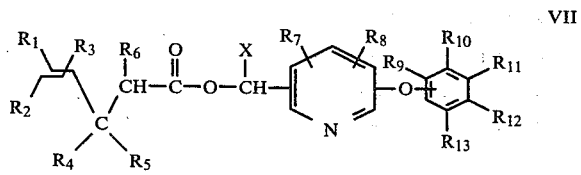

wherein:
R$^1$-R$^6$ and X are as described previously
R$^7$ may be hydrogen
R$^8$ may be hydrogen, branched or straight chain (C$_1$-C$_8$) alkoxy, or halogen
R$^7$ and R$^8$ may occupy adjacent carbons and may be joined by a carbon chain to complete a benzene ring fused to the pyridine nucleus.
R$^9$-R$^{13}$ may individually be hydrogen, halogen, alkyl, cycloalkyl, polyhaloalkyl, phenyl, phenoxy, alkoxy, alkynloxy, with no more than seven carbons in any one aliphatic chain. Any two substituents may be joined by an alkylene or polyhaloalkylene chain completing a 5, 6, or 7 membered ring or by a carbon chain completing a benzene ring fused to the phenoxy nucleus, with the proviso that:

(1) When R$^7$ and R$^8$ are hydrogen that either the 2- and 4- or the 2- and 6-positions of the pyridine nucleus are occupied by the phenoxy and acyloxymethyl radicals;

(2) When R$^7$ is hydrogen but R$^8$ is not hydrogen the 2-, 4- and 6-positions of the pyridine nucleus are occupied by R$^8$, the phenoxy and acyloxymethyl radicals; and (3) When R$^7$ and R$^8$ are joined to complete a benzene ring fused to the pyridine nucleus the 2- and 4-positions of a resulting quinoline or the 1- and 3-positions of a resulting isoquinoline are occupied by the phenoxy and acyloxymethyl radicals.

These compounds generalized by structure VI or VII with varying degrees of efficiency, are useful in combating insects and mites. In general, the compositions having the greatest degree of pesticidal activity are those in which only one of R$_4$ or R$_5$ is methyl. The preferred compositions of this invention are those in which R$_1$ and R$_2$ are halogen, preferably chlorine or bromine; wherein only one of R$_4$ or R$_5$ is methyl; and wherein R$_6$ is isopropyl or cyclopropyl.

It has been found that two halogens at the terminal end of the double bond (R$_1$ and R$_2$=halogen) provide pyrethroid esters having maximum activity. One or no halogens or methyl groups at the double bond terminus results in significantly lower biocidal activity. It has also been found that a halogen or methyl group at C$_4$ (R$_3$=halogen or methyl) results in a significant reduction in insecticidal activity. Maximum insecticidal activity is obtained when R$_3$=hydrogen.

Moreover, the insecticidal activity of the halo-4-alkenoic acid esters of this invention have been discovered to be critically dependent upon the substitution pattern at C$_3$, i.e., at R$_4$ and R$_5$. Table IV set forth subsequently herein illustrates that the variation in activity with substitution at C$_3$ can be seen to be in the order of CH$_3$—>H>CH$_3$CH$_2$—>gem- (CH$_3$)$_2$. Table IV also illustrates applicant's discovery that activity of halo-4-alkenoic acid esters on most insects may be remarkably enhanced with a single methyl substituent at C$_3$ (R$_4$ or R$_5$=CH$_3$). For example, when compared with a prior art halo-4-alkenoic acid esters having hydrogen substituents at C$_3$ such as disclosed in Belgium Pat. No. 860,687, an ester according to this invention which had a single methyl substituent at C$_3$ was found to be 10 times more active on the aphid and 8 times more active on the Mexican bean beetle.

The increase in activity with methyl substitution at C$_3$ in the halo-4-alkenoic acid esters of this invention is particularly surprising when compared to structure activity features observed with the alkenyl cyclopropanecarboxylates and the α-isopropyl acetates. See M. Elliot, *Synthesis Pyrethroids*, ACS Symposium Series 42, 1977, page 9. Pyrethroid esters of structure VIII show a high level of broad spectrum insecticidal activity but methyl substitution at C$_3$ to give structure IX results in complete loss of activity.

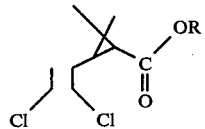

VIII

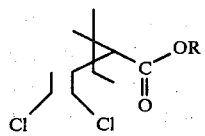

IX

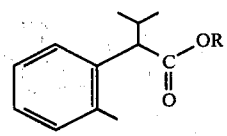

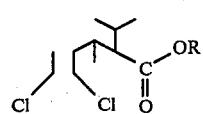

Esters of α-isopropylphenylacetic acid also exhibit a high level of insecticidal activity, but ortho substituents on the aryl ring, as in structure X, afford substantially reduced activity. The structural similarity of the active haloalkenoic acid ester of structure XI to the inactive compounds of structures IX and X provides a sharp contrast which further indicates the unexpected increased activity of applicant's pyrethroid esters. Also, when more than one methyl group is substituted at $C_3$, insecticidal activity has been found to decrease.

When a methyl group is present at $C_3$, the preferred substituent ($R_6$) at $C_2$ is a small substituent such as ethyl, cyclopropyl, isopropyl or the like, Isopropyl and cyclopropyl substituents at $C_2$ were found to be equivalent in activity on all insects tested except the armyworm. For worm activity, the preferred substituent at $C_2$ with a methyl group at $C_3$ is cyclopropyl>ethyl>isopropyl. The preferred substitution patterns at $C_2$ and $C_3$ have been found to be clearly related and cannot be viewed as isolated sites in any analysis of structure activity features. The degree of steric bulk at $C_2$ and $C_3$ is critical to the efficacy of the receptor site interaction for halo 4-alkenoic acid esters of this invention.

The esters according to the invention exhibit broad spectrum insecticidal and miticidal activity and are relatively safe to plants and mammals, i.e., low toxicity to mammals and little or no phytotoxicity.

The esters of this invention may be prepared by any of several methods which involve reacting an alcohol of the formula XII with an acid of the formula XIII:

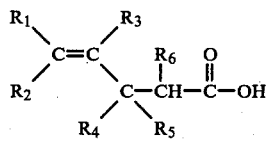    XIII or a reactive derivative thereof, wherein $R_1$–$R_{14}$ are as defined hereinabove for structure VI. The term reactive derivative of the acid refers to an acid halide, an acid anhydride, an ester with an alcohol having a low boiling point, an alkali metal salt, a silver salt, or an organic tertiary amine base salt of the acid. In certain instances, the halide or sulfoxylate derived from the alcohol

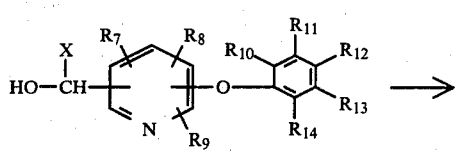    XII may be reacted with the acid derivative. These methods are illustrated by the general equations shown below:

Method 1

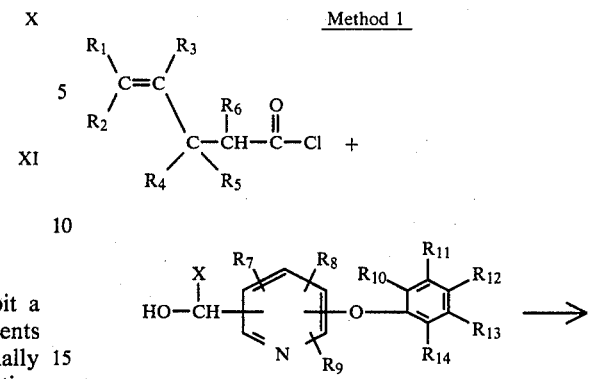

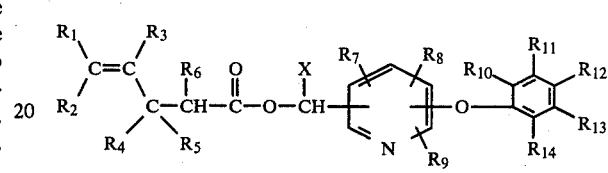

The acid halide is obtained by reacting the corresponding carboxylic acid with thionyl chloride, phosphorus trichloride, etc. The desired ester can be obtained in high yield by reacting the alcohol and the acid halide at room temperature using a proton acceptor, for example, an organic tertiary amine such as pyridine, triethylamine, and the like. The acid halides which can be used in the process of this invention may be acid fluorides, bromides, or chlorides, but an acid chloride is generally preferred. The presence of an inert solvent in the esterification is not essential, but it is generally preferred to use an inert solvent to assure a smooth reaction in this step. Any solvent may be used which is inert to the reactants and the ester product. Preferred solvents include benzene, toluene, carbon tetrachloride, methylene chloride, chloroform, and the like.

Optionally, in method 1 the acid anhydride may be used in place of the acid halide.

Method 2

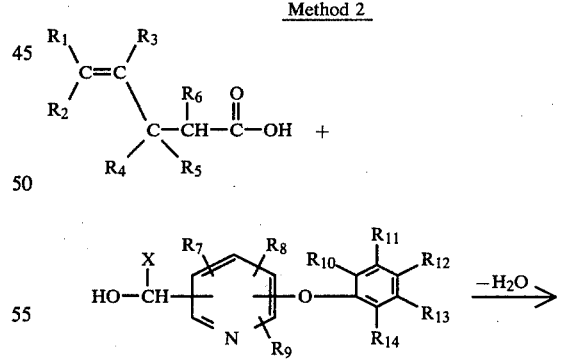

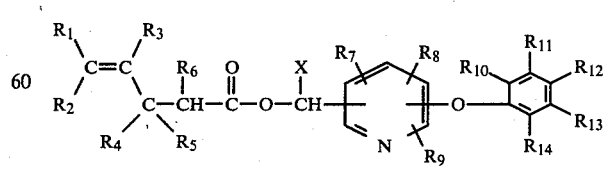

The esters of this invention may be prepared by reacting the carboxylic acids with the alcohols in an appropriate inert solvent at room temperature or an elevated temperature under an appropriate dehydrating condition, e.g., dicyclohexylcarbodiimide. Suitable solvents for this method are ether, toluene, benzene, carbon tetrachloride, methylene chloride, hexane, and the like.

Method 3

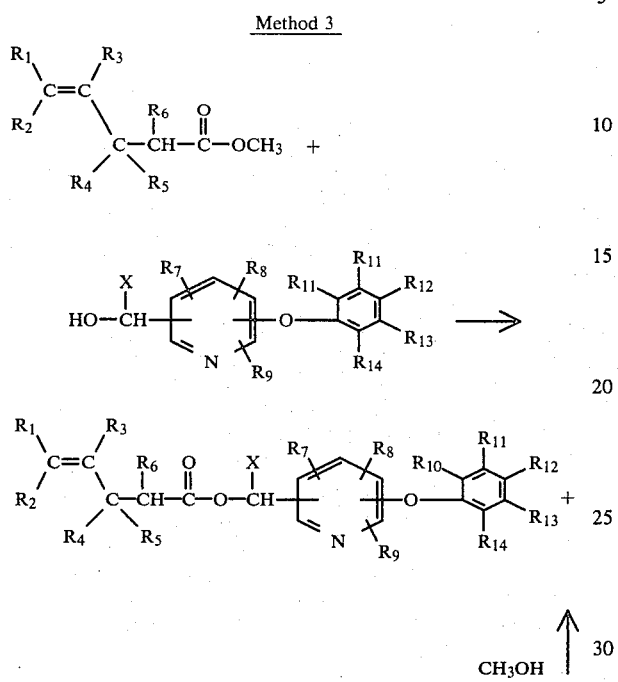

CH₃OH

When the alcohol is stable to strong base, the desired esters may be obtained by refluxing a low boiling point alcohol ester of the acid in the presence of an appropriate organic base catalyst in an inert solvent while removing the low boiling alcohol liberated in the reaction by azeotropic distillation. The base should be the alkali metal alkoxide corresponding to the low boiling alcohol of the ester used or an alkali metal hydride, e.g. sodium or lithium hydride. Preferred solvents for this method are toluene or benzene.

When a halide or sulfoxylate analog of the alcohol is used, the carboxylic acid is generally employed in the form of an alkali metal salt, a silver salt, or an organic tertiary amine base salt. These salts may be formed in situ by adding simultaneously the carboxylic acid and the corresponding base to the reaction mixture. In this case, a solvent such as toluene, benzene, acetone, dimethylsulfoxide, dimethylformamide, and the like is preferred, and the reaction is preferably conducted by heating the reaction mixture at or below the boiling point of the solvent used. Methods 4 and 5 below are illustrative of the processes described above.

Method 4

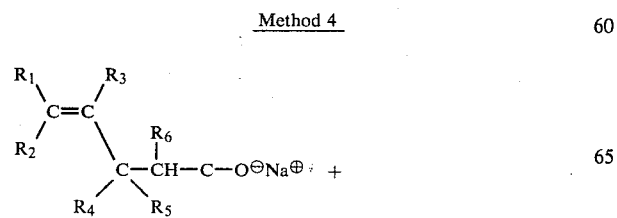

-continued

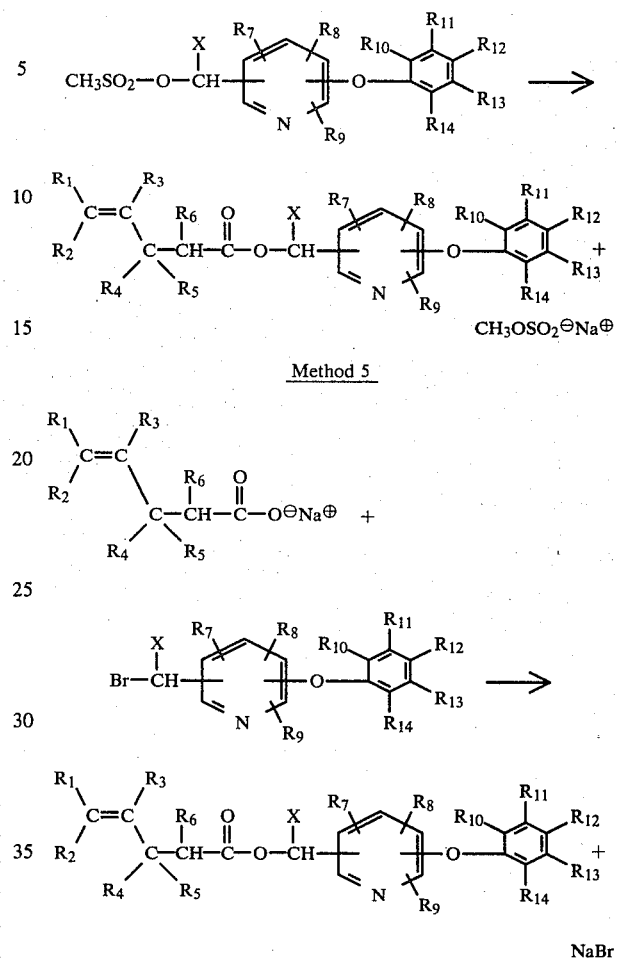

An especially active series of esters are those prepared from α-cyano-6-phenoxy-2-pyridinemethanol. These esters can be conveniently prepared as shown in method 6.

Method 6

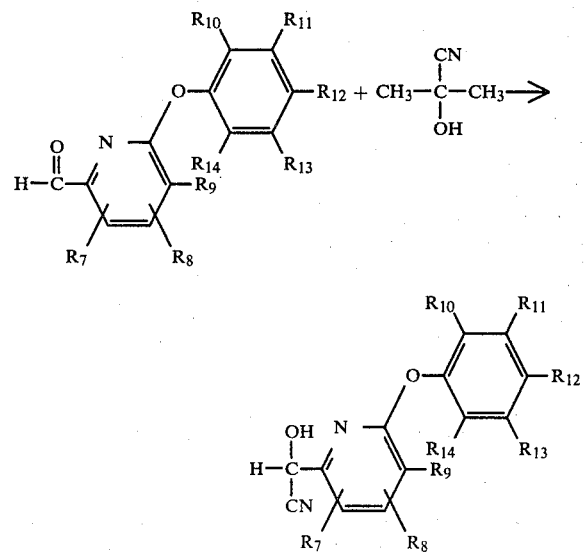

-continued
Method 6

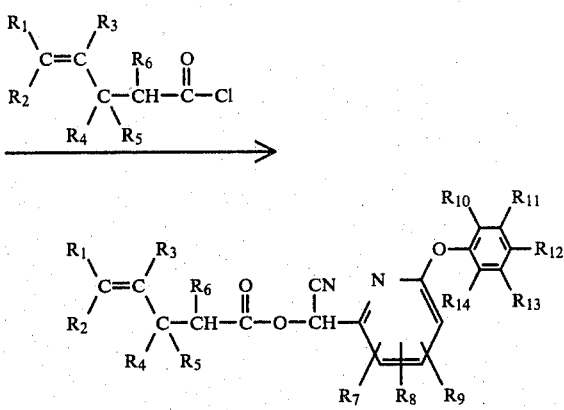

In method 6 the pyridine aldehyde accepts hydrogen cyanide from the donor, acetone cyanohydrin, to give the desired pyridine cyanohydrin in solution. The acid chloride and a proton acceptor, e.g. pyridine, are then added to the pyridine cyanohydrin solution to give the desired pyridinemethyl esters in good yield.

In the first step of method 6 a proton acceptor, e.g. triethylamine, is required in catalytic amounts to effect the hydrogen cyanide transfer. Method 6 is neither pressure nor temperature sensitive and may be run over a wide range of these variables. A preferred reaction condition is room temperature and autogenous pressure.

Another method by which the α-cyanopyridine methanols can be prepared is shown in method 7.

Method 7

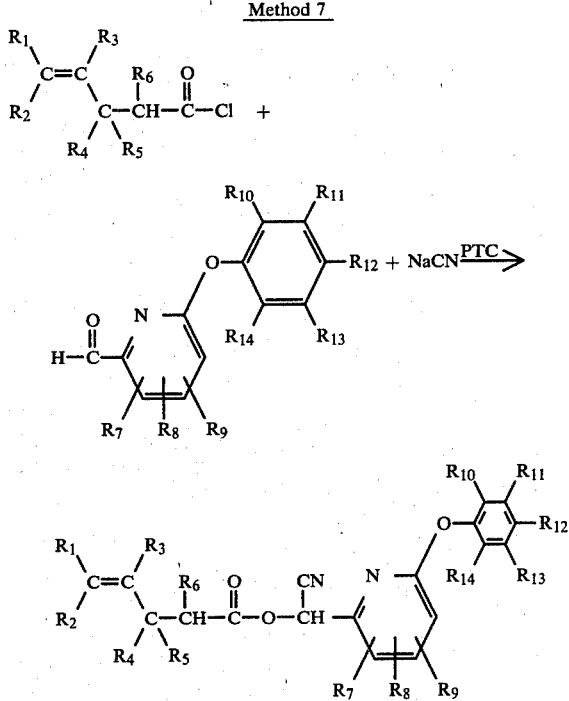

The process illustrated above as method 7 utilizes from 1.0 to 1.1 molar equivalents of the pyridine aldehyde, 1.0 molar equivalents of the acid chloride, and 1.1 to 1.5 molar equivalents of sodium cyanide. The phase transfer catalyst is employed in 0.01–0.10 molar equivalent amounts. In general, larger quantities of the PTC result in shorter reaction times.

Suitable phase transfer catalysts for method 7 are methyltricaprylammonium chloride, benzyltriethylammonium chloride, hexadecyltributylphosphonium bromide, tetra-n-butylammonium hydrogen sulfate, tetra-n-butylammonium chloride, trioctylpropylammonium chloride, and the like.

Method 7 is neither pressure nor temperature sensitive and may be conducted over a wide range of these variables. A preferred reaction condition is room temperature and autogenous pressure.

The carboxylic acids used to prepare the esters of this invention are synthesized by several methods which are described in detail in U.S. patent application, Ser. No. 054,209, filed July 2, 1979, entitled "Novel Halo-4-Alkenoic Acids and Their Use as Pesticidal Intermediates", the disclosure of which is incorporated herein by reference. Examples I and II below are typical examples representative of the methods used to prepare the acids utilized as intermediates in this invention. Examples III and IV below are representative examples of the methods used to prepare the alcohols used as intermediates in the preparation of the esters of this invention.

EXAMPLES

Example I: 5,5-dichloro-2-isopropyl-4-pentenoic acid

Part A: diethyl isopropyl-(3,3-dichloro-2-propenyl)malonate

A 1 liter flask was equipped with a mechanical stirrer, reflux condenser, addition funnel, thermometer, and nitrogen inlet. The flask was charged with 20.06 g (0.418 mol) of 50% sodium hydride dispersion in mineral oil. The oil was washed off the sodium hydride with two 50 ml portions of toluene, then 200 ml of toluene added to the flask and the mixture warmed to 50° C. To the reaction mixture was added dropwise 84.54 g (0.418 mol) of diethyl isopropylmalonate. If the evolution of hydrogen gas was not observed after a few grams of diethyl isopropylmolonate had been added, then a few drops of absolute ethanol were added to initiate the reaction. When all of the diethyl isopropylmalonate had been added, then a few drops of absolute ethanol were added to initiate the reaction. When all of the diethyl isopropylmalonate had been added, the reaction mixture was warmed to 75° C. until the evolution of hydrogen gas gas had cesed. While maintaining the temperature at 75° C., 60.78 g (0.418 mol) of 1,1,3-trichloropropene was added dropwise. When all the halide had been added, the reaction mixture was refluxed overnight. The reaction mixture was then cooled to room temperature, and 25 ml of ice water added dropwise. The reaction mixture was poured into 500 ml of ice water, and extracted into ether. The combined ether extracts were washed twice with water, dried (MgSO4), and the ether removed. The residue was vacuum distilled through a vigreux column to give 111.7 g (86% yield) of the desired malonate, b.p. 115°–130° C./0.20 mm.

IR(neat, cm$^{-1}$): 2970(s), 2930(m), 2900(m), 2880(m), 1730(s), 1620(m), 1550(m), 1500(m), 1390(m), 1370(m), 1320(w), 1270(m), 1230(s), 1195(s), 1130(m), 1095(m), 1040(m), 915(w), 895(w), 880(w), 855(m).

NMR(CDCl3, δ): 1.02 (d,6H); 1.29(t,6H); 2.30(m,1H); 2.75(d,2H); 4.20(q,4H); 5.95(t,1H).

Part B: ethyl 5,5-dichloro-2-isopropyl-4-pentenoate

A 1 liter flask was charged with 100.0 g (0.350 mol) of diethyl isopropyl (3,3-dichloro-2-propenyl)malonate, 36.05 g (0.350 mol) of sodium bromide, 12.92 g (0.70 mol) of water, and 269 ml of dimethylsulfoxide. The reaction mixture was heated to 185°–190° C. (oil bath temperature) until no evolution of $CO_2$ was observed. The reaction mixture (dark colored) was cooled to room temperature and poured into three times its volume of water. This mixture was extracted four times with 150 ml portions of ether. The combined ether extracts were washed twice with water, dried ($MgSO_4$), and the ether removed. The residue was vacuum distilled through a vigreux column to give 70.5 g (84% yield) of ethyl 5,5-dichloro-2-isopropyl-4-pentenoate, bp 72°–77°/0.20 mm.

NMR($CDCl_3$, δ): 0.95 (d,6H); 1.20(t,3H); 1.94(m,1H); 2.37(m,3H); 4.15(q,2H); 5.87(t,1H).

Part C: 5,5-dichloro-2-isopropyl-4-pentenoic acid

A mixture of 67.0 g (0.28 mol) of ethyl 5,5-dichloro-2-isopropyl-4-pentenoate, 77.35 g (0.56 mol) of anhydrous potassium carbonate, 2128 ml of methanol, and 708 ml of water was refluxed 4 days under nitrogen. The reaction mixture was then cooled to room temperature and about two-thirds of the solvent removed on the rotary evaporator. The residue was taken up in three times its volume of water, extracted twice with ether, and acidified with conc. HCl. The acidified reaction mixture was extracted into ether, the ether solution washed with water, dried ($MgSO_4$), and removed. The residue was vacuum distilled to give 52.5 g (89% yield) of 5,5-dichloro-2-isopropyl-4-pentenoic acid, b.p. 91°–96° C./0.30 mm.

NMR($CDCl_3$, δ): 0.95 (d,6H); 2.0 (m,1H); 2.35(m,3H); 5.85 (m,1H); 11.9(s,1H).

Example II:
5,5-dichloro-3-methyl-2-isopropyl-4-pentenoic acid

Part A: 1-trimethylsilyloxy-1-ethoxy-3-methyl-1-butene

A 1 liter flask was equipped with a mechanical stirrer, a reflux condenser, an addition funnel, nitrogen inlet, and thermometer. The glassware was dried carefully and charged with 225 ml of tetrahydrofuran, 30.36 g (0.300 mol) of diisopropylamine, and cooled to 0° C. Over a 30 minute period, 190 ml (0.300 mol) of 1.6 M n-butyl lithium in hexane was added. The reaction mixture was stirred at 0° C. for 15 min., then cooled to −76° C. and 39.06 g (0.300 mol) of ethyl isovalerate added dropwise over ~15 min. When addition was complete, the reaction mixture was stirred for 15 min. at −76° C., then 82 ml (0.88 mol) of chlorotrimethylsilane added dropwise. When addition was complete, the Dry Ice-acetone bath was removed and the reaction mixture stirred for 1½ hrs. while coming up to room temperature.

The reaction mixture was filtered and concentrated under reduced pressure. The residue was taken up in ether and filtered. The filtrate was concentrated on the rotary evaporator, then vacuum distilled through a vigreux column to give 52.29 g (86% yield) of the desired ketene acetal, b.p. 79°–86° C./31 mm.

NMR ($CDCl_3$, δ): 0.22 (s,9H); 0.95 (d,6H); 1.21 (t,3H); 2.50 (m,1H); 3.76(m,2H).

Part B: ethyl 5,5-dichloro-3-methyl-2-isopropyl-4-pentenoate

A 250 ml R.B. flask was equipped with a magnetic stirrer, reflux condenser, and $N_2$ inlet tube. The glassware was dried thoroughly then charged with 23.91 g (0.15 mol) of 1,1,3-trichloro-1-butene, 30.36 g (0.15 mol) of 1-trimethylsilyloxy-1-ethoxy-3-methyl-1-butene, 100 ml of methylene chloride, and ~0.50 g of anhydrous zinc chloride. The reaction mixture was stirred at room temperature and monitored by infrared. The gradual disappearance of the ketene acetal C=C peak at 1675 $cm^{-1}$ and the appearance of an ester C=O peak at 1720 $cm^{-1}$ was observed. The reaction mixture after 67 hours showed only a c=O peak at 1720 $cm^{-1}$ and no 1675 $cm^{-1}$, and was diluted with 150 ml of methylene chloride, washed with 5×100 ml of 5% sodium bicarbonate solution, then 2× with 50 ml of water. The methylene chloride was dried ($MgSO_4$), stripped, and the residue vacuum distilled through a vigreux column to give 23.41 g (62% yield) of the desired product, b.p. 64°–68° C./0.30 mm.

Part C: 5,5-dichloro-3-methyl-2-isopropyl-4-pentenoic acid

A solution of 23.41 g (0.0925 mol) of ethyl 5,5-dichloro-3-methyl-2-isopropyl-4-pentenoate, 11.10 g (0.278 mol) of sodium hydroxide, 40 ml of water, and 40 ml of ethanol was refluxed for 3 days under $N_2$, the solvent was concentrated on the rotary evaporator, the residue taken up in 300 ml of water and extracted 2× with ether. The aqueous layer was acidified with conc. HCl, then extracted 3× with 150 ml of ether. The combined ether extracts were washed with water, dried ($MgSO_4$), and stripped to give 17.09 g (82% yield) of the desired acid.

NMR ($CDCl_3$, δ): 1.08(m,9H); 2.10(m,2HO; 2.90(m,1H); 5.70 and 6.20(d,pair, 1H); 10.75(s,1H).

Example III: 6-Phenoxy-2-pyridinemethanol

Part A: 6-Bromo-2-picoline

To 585 ml of 47% HBr solution under an atmosphere of nitrogen and cooled to −5° C. (internal) was slowly added 100 g of 6-amino-2-picoline. To the resulting solution was then added 143 ml of bromine at such a rate to maintain the internal temperature below 10° C. After this addition was complete, a solution containing 175 g of sodium nitrite dissolved in 250 ml $H_2O$ was added at such a rate to maintain the internal temperature below 10° C. After the addition was complete, this mixture was stirred for 1 hr. below 5° C. (internal). To this reaction mixture was then added a solution containing 375 g of NaOH dissolved in 950 ml $H_2O$ at such a rate to maintain the internal temperature below 30° C. The crude reaction mixture was then extracted with ether. The combined etheral extracts were washed twice with $H_2O$ and once with saturated brine. After drying over anhydrous $Na_2SO_4$, removal of the solvents in vacuo afforded 132.1 g of dark brown oil. Distillation afforded 108.42 g of pale yellow oil, b.p. 95°–98° C. at 15 mm Hg.

Part B: 6-Phenoxy-2-picoline

A mixture containing 50.28 g of 6-bromo-2-picoline, 83.01 g of phenol and 120.86 g of potassium carbonate under an atmosphere of nitrogen was heated in an oil bath maintained at 210° C. for 20 hrs. After cooling to room temperature, the reaction mixture was dissolved in 1000 ml of $H_2O$ and 500 ml of ether. The layers were then separated and the aqueous layer extracted with ether. The combined etheral extracts were washed three times with 5% NaOH and then once with $H_2O$. After drying the etheral layer over anhydrous $Na_2SO_4$, removal of the solvents afforded 67.3 g of an orange oil. Distillation afforded 44.32 g of colorless oil, b.p. 80°–85° at 5 mm.

Part C: 6-Phenoxy-2-picoline N-oxide

To a solution containing 44.11 g of 6-phenoxy-2-picoline dissolved in 825 ml of methylene chloride under an atmosphere of nitrogen and at room temperature was added 96.82 g of 85% m-chloro-peroxybenzoic acid. The resulting mixture was stirred for 18 hrs. under an atmosphere of nitrogen and at room temperature. The reaction mixture was transferred to a separatory funnel and washed three times with 10% $Na_2CO_3$ twice with $H_2O$ and finally with saturated brine. After drying over anhydrous $Na_2SO_4$ removal of the solvents afforded 37.80 g of yellow oil. This material was used without purification in Part D.

Part D: 6-Phenoxy-2-pyridinemethyl acetate

To a mixture of 28.51 g of sodium acetate in 100 ml of acetic anhydride under an atmosphere of nitrogen and at reflux was added a solution containing 46.19 g of the crude 6-phenoxy-2-picoline N-oxide dissolved in 85 ml of acetic anhydride. After the addition was complete, the reaction mixture was refluxed for an additional 2 hrs. The solution was cooled to room temperature and filtered. The collected salts were thoroughly washed with ether. The solvents were then removed in vacuo. The resulting residue was taken up in 200 ml ether and washed with 5% NaOH and then $H_2O$. After drying over anhydrous $Na_2SO_4$, removal of the solvents afforded 51.13 g of a dark brown oil. Distillation afforded 27.85 g of the desired acetate as a colorless oil, b.p. 128°–132° C. at 0.075 mm.

Part E: 6-Phenoxy-2-Pyridinemethyl alcohol

To a solution containing 20.0 g of KOH and 100 ml of $H_2O$ in 200 ml ethanol was added 24.7 g of 6-phenoxy-2-pyridinemethyl acetate. The resulting solution was refluxed under an atmosphere of nitrogen for 3 hrs. After cooling to room temperature, 200 ml of $H_2O$ was added. The resulting solution was extracted three times with $CHCl_3$. The combined extracts were dried over anhydrous $Na_2SO_4$. Removal of the solvents afforded 21.40 g of the desired alcohol as an oil. This material could be utilized without further purification or purified through chromatography on silica gel.

Analysis Calc. for $C_{12}H_{11}NO_2$ C, 71.71; H, 5.52; N, 6.97. Found: C, 71,51; H, 5.60; N, 6.91.

Example IV: 6-Phenoxypyridine-2-carboxaldehyde

A solution containing 21.0 ml of dry DMSO in 150 ml of dry $CH_2Cl_2$ under an atmosphere of nitrogen was cooled to −75° (internal). To this reaction mixture was then added 31.0 g of trifluoroactic anhydride at such a rate to maintain the temperature below −60° (internal). After the addition was complete the reaction mixture was stirred at −75° for 20 min. To the resulting mixture was added a solution containing 29.25 g of 6-phenoxypyridine-2-pyridinemethanol in 150 ml $CH_2Cl_2$. During this addition the internal temperature was not allowed to rise above −60° C. After stirring this reaction mixture for 1 hr. at −75° C., 90 ml of triethylamine was added. The cooling bath was removed and the reaction mixture was allowed to warm to room temperature. The reaction mixture was diluted with 1 L of ether and washed four times with $H_2O$. After drying over anhydrous $Na_2SO_4$, removal of the solvents afforded 29.31 g of dark oil. This material was treated with decolorizing carbon and recrystallized from hexane-ethyl acetate to afford 21.50 g of the desired crystalline aldehyde.

m.p. 58°–59° C. NMR ($CDCl_3$) δ6.4–8.0 (m,8H), 9.89 (s,1H)

Example V: (6-Phenoxy-2-pyridinemethyl)5,5-dichloro-2-isopropyl-4-pentenoate

A 100 ml flask equipped with an addition funnel, magnetic stirrer, and $N_2$ inlet tube was dried thoroughly and charged with 3.32 g (0.0157 mol) of 5,5-dichloro-2-isopropyl-4-pentenoic acid, 30 ml of carbon tetrachloride, and 4 drops of pyridine. The mixture was cooled in an ice bath and the thionyl chloride (3.73 g, 0.0314 mol) added over ∼10 minutes. The mixture was refluxed for 2 hrs, the solvent and excess thionyl chloride removed on the rotary evaporator, 30 ml of $CCl_4$ added and the solution filtered into an addition funnel through a glass wool plug.

A 100 ml flask equipped with magnetic stirrer, $N_2$ inlet, and addition funnel was charged with 2.87 g (0.0143 mol) of 2-hydroxymethyl-6-phenoxypyridine, 20 ml of $CCl_4$, and 1.98 g (0.0196 mol) of triethylamine, and cooled in an ice bath. The acid chloride was added dropwise, the reaction mixture stirred at 0° C. for 1 hr. and room temperature for 16 hrs. The $CCl_4$ was removed on the rotary evaporator, the residue triturated with ether and filtered, and the filtrate washed with water, 10% $NaHCO_3$, and water. The ether solution was dried ($MgSO_4$), filtered through activated charcoal, and the ether removed to give 5.7 g of colorless oil.

This oil was chromatographed through silica gel using 95:5 hexane-ethyl acetate. A total of 4.32 g (77% yield) of the desired product was obtained as a clear, colorless oil.

| Anal. | % C | % H | % N |
|---|---|---|---|
| Calcd. | 60.92 | 5.37 | 3.55 |
| Found | 61.13 | 5.14 | 3.57 |

Example VI: [6-phenoxy-2-(α-cyanopyridinemethyl)] 5,5-dichloro-2-cyclopropyl-4-pentenoate A 100 ml flask equipped with an addition funnel, magnetic stirrer, and $N_2$ inlet tube was dried thoroughly and charged with 3.00 g (0.0144 mol) of 5,5-dichloro-2-cyclopropyl-4-pentenoic acid, 30 ml of carbon tetrachloride, and 4 drops of pyridine. The mixture was cooled in an ice bath and 3.40 g (0.0288 mol) of thionyl chloride added. The mixture was refluxed for 2 hrs., the solvent and excess thionyl chloride removed on the rotary evaporator, 30 ml of $CCl_4$ added, and the solvent stripped again. The residue was taken up in 10 ml of $CCl_4$ and placed into an addition funnel.

A 100 ml R.B. flask was equipped with a magnetic stirrer and $N_2$ inlet. The flask was charged with 2.84 g (0.0142 mol) of 6-phenoxy-2-pyridine-carboxyaldehyde, 1.43 ml (0.0156 mol) of acetone cyanohydrin, 15 ml of $CCl_4$, and 5 drops of triethylamine. The reaction mixture was stirred at room temperature and monitored by nmr. When the aldehyde peak at 9.89δ had disappeared, the reaction mixture was cooled to 0° C. in an ice bath, and the acid chloride solution added. Then 2.0 ml of pyridine was added, and the reaction mixture stirred at 0° C. for 30 min., then allowed to come to room temperature and stirred overnight.

The reaction mixture was taken up in 100 ml of CCl₄, washed with 50 ml of water, then 2×75 ml of 2% HCl, then 2× with water. The CCl₄ solution was dried (MgSO₄), and the solvent removed to leave a yellow oil 6.58 g. This oil was purified by chromatography through a silica gel using 95:5 hexane-ethyl acetate. A total of 3.39 g (56%) of a pale yellow oil was obtained as the desired product.

| Anal. | % C | % H | % N |
|---|---|---|---|
| Calcd. | 60.45 | 4.35 | 6.71 |
| Found | 60.73 | 4.24 | 6.62 |

All of the compounds whose physical properties are summarized in Table I discussed subsequently herein were prepared using the general procedure given in Examples I and II.

The following novel phenoxypyridinemethyl esters disclosed herein in addition to those described in Examples V and VI are illustrative of the new compositions of this invention:

6-(4-chlorophenoxy)-2-pyridinemethyl 5,5-dichloro-2-isopropyl-3-methyl-4-pentenoate α-cyano-6-(4-chlorophenoxy)-2-pyridinemethyl 5,5-dichloro-2-isopropyl-3-methyl-4-pentenoate α-ethynyl-6-(4-chlorophenoxy)-2-pyridinemethyl 5,5-dichloro-2-isopropyl-3-methyl-4-pentenoate α-thiamido-6-(4-chlorophenoxy)-2-pyridinemethyl 5,5-dichloro-2-isopropyl-3-methyl-4-pentenoate α-cyano-6-(4-chlorophenoxy)-2-pyridinemethyl 5,5-dichloro-2-isopropyl-4-pentenoate α-ethynyl-6-(4-chlorophenoxy)-2-pyridinemethyl 5,5-dichloro-2-isopropyl-4-pentenoate α-thiamido-6-(4-chlorophenoxy)-2-pyridinemethyl 5,5-dichloro-2-isopropyl-4-pentenoate 6-(4-chlorophenoxy)-2-pyridinemethyl 5,5-dibromo-2-isopropyl-4-pentenoate α-cyano-6-(4-chlorophenoxy)-2-pyridinemethyl 5,5-dibromo-2-isopropyl-4-pentenoate α-ethynyl-6-(4-chlorophenoxy)-2-pyridinemethyl 5,5-dibromo-2-isopropyl-4-pentenoate α-thiamido-6-(4-chlorophenoxy)-2-pyridinemethyl 5,5-dibromo-2-isopropyl-4-pentenoate α-ethynyl-6-phenoxy-2-pyridinemethyl 5,5-dichloro-2-isopropyl-3-methyl-4-pentenoate α-thiamido-6-phenoxy-2-pyridinemethyl 5,5-dichloro-2-isopropyl-3-methyl-4-pentenoate α-ethynyl-6-phenoxy-2-pyridinemethyl 5,5-dichloro-2-isopropyl-4-pentenoate α-thiamido-6-phenoxy-2-pyridinemethyl 5,5-dichloro-2-isopropyl-4-pentenoate α-cyano-6-phenoxy-2-pyridinemethyl 5,5-dibromo-2-isopropyl-4-pentenoate α-ethynyl-6-phenoxy-2-pyridinemethyl 5,5-dibromo-2-isopropyl-4-pentenoate α-thiamido-6-phenoxy-2-pyridinemethyl 5,5-dibromo-2-isopropyl-4-pentenoate 6-(4-fluorophenoxy)-2-pyridinemethyl 5,5-dichloro-2-isopropyl-3-methyl-4-pentenoate α-cyano-6-(4-fluorophenoxy)-2-pyridinemethyl 5,5-dichloro-2-isopropyl-3-methyl-4-pentenoate α-ethynyl-6-(4-fluorophenoxy)-2-pyridinemethyl 5,5-dichloro-2-isopropyl-3-methyl-4-pentenoate α-thiamido-6-(4-fluorophenoxy)-2-pyridinemethyl 5,5-dichloro-2-isopropyl-3-methyl-4-pentenoate 6-(4-fluorophenoxy)-2-pyridinemethyl 5,5-dichloro-2-isopropyl-4-pentenoate α-cyano-6-(4-fluorophenoxy)-2-pyridinemethyl 5,5-dichloro-2-isopropyl-4-pentenoate α-ethynyl-6-(4-fluorophenoxy)-2-pyridinemethyl 5,5-dichloro-2-isopropyl-4-pentenoate α-thiamido-6-(4-fluorophenoxy)-2-pyridinemethyl 5,5-dichloro-2-isopropyl-4-pentenoate 6-(4-fluorophenoxy)-2-pyridinemethyl 5,5-dibromo-2-isopropyl-4-pentenoate α-cyano-6-(4-fluorophenoxy)-2-pyridinemethyl 5,5-dibromo-2-isopropyl-4-pentenoate α-ethynyl-6-(4-fluorophenoxy)-2-pyridinemethyl 5,5-dibromo-2-isopropyl-4-pentenoate α-thiamido-6-(4-fluorophenoxy)-2-pyridinemethyl 5,5-dibromo-2-isopropyl-4-pentenoate α-ethynyl-6-(4-ethoxyphenoxy)-2-pyridinemethyl 5,5-dichloro-2-isopropyl-3-methyl-4-pentenoate α-cyano-6-(4-ethoxyphenoxy)-2-pyridinemethyl 5,5-dichloro-2-isopropyl-3-methyl-4-pentenoate 6-(4-ethoxyphenoxy)-2-pyridinemethyl 5,5-dichloro-2-isopropyl-3-methyl-4-pentenoate α-thiamido-6-(4-ethoxyphenoxy)-2-pyridinemethyl 5,5-dichloro-2-isopropyl-3-methyl-4-pentenoate 6-(4-ethoxyphenoxy)-2-pyridinemethyl 5,5-dichloro-2-isopropyl-4-pentenoate α-cyano-6-(4-ethoxyphenoxy)-2-pyridinemethyl 5,5-dichloro-2-isopropyl-4-pentenoate α-ethynyl-6-(4-ethoxyphenoxy)-2-pyridinemethyl 5,5-dichloro-2-isopropyl-4-pentenoate α-thiamido-6-(4-ethoxyphenoxy)-2-pyridinemethyl 5,5-dichloro-2-isopropyl-4-pentenoate 6-phenoxy-2-pyridinemethyl 5,5-dichloro-3-ethyl-2-isopropyl-4-pentenoate 6-(4-fluorophenoxy)-2-pyridinemethyl 5,5-dichloro-3-ethyl-2-isopropyl-4-pentenoate 6-(4-ethoxyphenoxy)-2-pyridinemethyl 5,5-dichloro-3-ethyl-2-isopropyl-4-pentenoate α-cyano-6-(4-fluorophenoxy)-2-pyridinemethyl 5,5-dichloro-3-ethyl-2-isopropyl-4-pentenoate α-cyano-6-phenoxy-2-pyridinemethyl 5,5-dichloro-3-ethyl-2-isopropyl-4-pentenoate α-cyano-6-(4-ethoxyphenoxy)-2-pyridinemethyl 5,5-dichloro-3-ethyl-2-isopropyl-4-pentenoate α-ethynyl-6-phenoxy-2-pyridinemethyl 5,5-dichloro-3-ethyl-2-isopropyl-4-pentenoate α-ethynyl-6-(4-ethoxyphenoxy)-2-pyridinemethyl 5,5-dichloro-3-ethyl-2-isopropyl-4-pentenoate α-ethynyl-6-(4-fluorophenoxy)-2-pyridinemethyl 5,5-dichloro-3-ethyl-2-isopropyl-4-pentenoate α-ethynyl-6-(4-chlorophenoxy)-2-pyridinemethyl 5,5-dichloro-3-ethyl-2-isopropyl-4-pentenoate α-ethynyl-6-(4-chlorophenoxy)-2-pyridinemethyl 5,5-dichloro-3-ethyl-2-isopropyl-4-pentenoate 6-(4-chlorophenoxy)-2-pyridinemethyl 5,5-dichloro-3-ethyl-2-isopropyl-4-pentenoate α-cyano-6-(4-chlorophenoxy)-2-pyridinemethyl 5,5-dichloro-3-ethyl-2-isopropyl-4-pentenoate α-thiamido-6-phenoxy-2-pyridinemethyl 5,5-dichloro-3-ethyl-2-isopropyl-4-pentenoate α-thiamido-6-(4-fluorophenoxy)-2-pyridinemethyl 5,5-dichloro-3-ethyl-2-isopropyl-4-pentenoate α-thiamido-6-(4-ethoxyphenoxy)-2-pyridinemethyl 5,5-dichloro-3-ethyl-2-isopropyl-4-pentenoate
α-thiamido-6-(4-chlorophenoxy)-2-pyridinemethyl 5,5-dichloro-3-ethyl-2-isopropyl-4-pentenoate
6-phenoxy-2-pyridinemethyl 5,5-dichloro-2,3-diisopropyl-2-pentenoate
6-(4-fluorophenoxy)-2-pyridinemethyl 5,5-dichloro-2,3-diisopropyl-4-pentenoate
6-(4-ethoxyphenoxy)-2-pyridinemethyl 5,5-dichloro-2,3-diisopropyl-4-pentenoate
6-(4-chlorophenoxy)-2-pyridinemethyl 5,5-dichloro-2,3-diisopropyl-4-pentenoate
α-cyano-6-phenoxy-2-pyridinemethyl 5,5-dichloro-2,3-diisopropyl-4-pentenoate
α-cyano-6-(4-fluorophenoxy)-2-pyridinemethyl 5,5-dichloro-2,3-diisopropyl-4-pentenoate
α-cyano-6-(4-ethoxyphenoxy)-2-pyridinemethyl 5,5-dichloro-2,3-diisopropyl-4-pentenoate
α-cyano-6-(4-chlorophenoxy)-2-pyridinemethyl 5,5-dichloro-2,3-diisopropyl-4-pentenoate
α-ethynyl-6-phenoxy-2-pyridinemethyl 5,5-dichloro-2,3-diisopropyl-4-pentenoate
α-ethynyl-6-(4-fluorophenoxy)-2-pyridinemethyl 5,5-dichloro-2,3-diisopropyl-4-pentenoate
α-ethynyl-6-(4-chlorophenoxy)-2-pyridinemethyl 5,5-dichloro-2,3-diisopropyl-4-pentenoate
α-ethynyl-6-(4-ethoxyphenoxy)-2-pyridinemethyl 5,5-dichloro-2,3-diisopropyl-4-pentenoate
α-thiamido-6-phenoxy-2-pyridinemethyl 5,5-dichloro-2,3-diisopropyl-4-pentenoate
α-thiamido-6-(4-fluorophenoxy)-2-pyridinemethyl 5,5-dichloro-2,3-diisopropyl-4-pentenoate
α-thiamido-6-(4-ethoxyphenoxy)-2-pyridinemethyl 5,5-dichloro-2,3-diisopropyl-4-pentenoate
α-thiamido-6-(4-chlorophenoxy)-2-pyridinemethyl 5,5-dichloro-2,3-diisopropyl-4-pentenoate
α-cyano-6-(4-methoxyphenoxy)-2-pyridinemethyl 5,5-dichloro-2-isopropyl-3-methyl-4-pentenoate
6-(4-methoxyphenoxy)-2-pyridinemethyl 5,5-dichloro-2-isopropyl-3-methyl-4-pentenoate
6-(4-tert-butylphenoxy)-2-pyridinemethyl 5,5-dichloro-2-isopropyl-3-methyl-4-pentenoate
α-cyano-6-(4-tert-butylphenoxy)-2-pyridinemethyl 5,5-dichloro-2-isopropyl-3-methyl-4-pentenoate
α-cyano-6-(4-methylphenoxy)-2-pyridinemethyl 5,5-dichloro-2-isopropyl-3-methyl-4-pentenoate
6-(4-methylphenoxy)-2-pyridinemethyl 5,5-dichloro-2-isopropyl-3-methyl-4-pentenoate
6-(1-napthoxy)-2-pyridinemethyl 5,5-dichloro-2-isopropyl-3-methyl-4-pentenoate)
α-cyano-6-(1-napthoxy)-2-pyridinemethyl 5,5-dichloro-2-isopropyl-3-methyl-4-pentenoate
α-ethynyl-6-(1-napthoxy)-2-pyridinemethyl 5,5-dichloro-2-isopropyl-3-methyl-4-pentenoate
6-(1-napthoxy)-2-pyridinemethyl 5,5-dichloro-2-isopropyl-4-pentenoate
α-cyano-6-(1-napthoxy)-2-pyridinemethyl 5,5-dichloro-2-isopropyl-4-pentenoate
α-ethynyl-6-(1-napthoxy)-2-pyridinemethyl 5,5-dichloro-2-isopropyl-4-pentenoate
α-cyano-6-(1-napthoxy)-2-pyridinemethyl 5,5-dibromo-2-isopropyl-4-pentenoate
6-(1-napthoxy)-2-pyridinemethyl 5,5-dichloro-3-ethyl-2-isopropyl-4-pentenoate
α-cyano-6-(1-napthoxy)-2-pyridinemethyl 5,5-dichloro-3-ethyl-2-isopropyl-4-pentenoate
α-ethynyl-6-(1-napthoxy)-2-pyridinemethyl 5,5-dichloro-3-ethyl-2-isopropyl-4-pentenoate
α-cyano-6-(2-napthoxy)-2-pyridinemethyl 5,5-dichloro-2,3-diisopropyl-4-pentenoate
α-cyano-6-(1-napthoxy)-2-pyridinemethyl 5,5-dichloro-2,3-diisopropyl-4-pentenoate
4-phenoxy-2-quinolinemethyl 5,5-dichloro-2-isopropyl-3-methyl-4-pentenoate
α-cyano-4-phenoxy-2-quinolinemethyl 5,5-dichloro-2-isopropyl-3-methyl-4-pentenoate
α-ethynyl-4-phenoxy-2-quinolinemethyl 5,5-dichloro-2-isopropyl-3-methyl-4-pentenoate
α-thiamido-4-phenoxy-2-quinolinemethyl 5,5-dichloro-2-isopropyl-3-methyl-4-pentenoate
4-phenoxy-2-quinolinemethyl 5,5-dichloro-3-ethyl-2-isopropyl-4-pentenoate
α-cyano-4-(4-fluorophenoxy)-2-quinolinemethyl 5,5-dichloro-2-isopropyl-4-pentenoate
α-ethynyl-4-(4-chlorophenoxy)-2-quinolinemethyl 5,5-dichloro-2,3-diisopropyl-4-pentenoate
α-thiamido-4-(4-ethoxyphenoxy)-2-quinolinemethyl 5,5-dibromo-2-isopropyl-4-pentenoate
2-phenoxy-4-quinolinemethyl 5,5-dichloro-2-isopropyl-3-methyl-4-pentenoate
α-cyano-2-phenoxy-4-quinolinemethyl 5,5-dichloro-2-isopropyl-3-methyl-4-pentenoate
α-ethynyl-2-phenoxy-4-quinolinemethyl 5,5-dichloro-2-isopropyl-3-methyl-4-pentenoate
α-thiamido-2-phenoxy-4-quinolinemethyl 5,5-dichloro-2-isopropyl-3-methyl-4-pentenoate
α-ethynyl-2-phenoxy-4-quinolinemethyl 5,5-dichloro-2-isopropyl-4-pentenoate
α-thiamido-2-(4-fluorophenoxy)-4-quinolinemethyl 5,5-dichloro-3-ethyl-2-isopropyl-4-pentenoate
2-(4-chlorophenoxy)-4-quinolinemethyl 5,5-dichloro-2,3-diisopropyl-4-pentenoate
α-cyano-2-(4-ethoxyphenoxy)-4-quinolinemethyl 5,5-dibromo-2-isopropyl-4-pentenoate
1-phenoxy-3-isoquinolinemethyl 5,5-dichloro-3-methyl-2-isopropyl-4-pentenoate
α-cyano-1-phenoxy-3-isoquinolinemethyl 5,5-dichloro-3-methyl-2-isopropyl-4-pentenoate
α-ethynyl-1-phenoxy-3-isoquinolinemethyl 5,5-dichloro-3-methyl-2-isopropyl-4-pentenoate
α-thiamido-1-phenoxy-3-isoquinolinemethyl 5,5-dichloro-2-isopropyl-3-methyl-4-pentenoate
α-thiamido-1-phenoxy-3-isoquinolinemethyl 5,5-dichloro-2-isopropyl-4-pentenoate
α-ethynyl-1-(4-fluorophenoxy)-3-isoquinolinemethyl 5,5-dichloro-3-ethyl-2-isopropyl-4-pentenoate
α-cyano-1-(4-chlorophenoxy)-3-isoquinolinemethyl 5,5-dichloro-2,3-diisopropyl-4-pentenoate
1-(4-ethoxyphenoxy)-3-isoquinolinemethyl 5,5-dibromo-2-isopropyl-4-pentenoate
3-phenoxy-1-isoquinolinemethyl 5,5-dichloro-2-isopropyl-3-methyl-4-pentenoate
α-cyano-3-phenoxy-1-isoquinolinemethyl 5,5-dichloro-2-isopropyl-3-methyl-4-pentenoate
α-ethynyl-3-phenoxy-1-isoquinolinemethyl 5,5-dichloro-2-isopropyl-3-methyl-4-pentenoate
α-thiamido-3-phenoxy-1-isoquinolinemethyl 5,5-dichloro-2-isopropyl-3-methyl-4-pentenoate
3-(4-fluorophenoxy)-1-isoquinolinemethyl 5,5-dichloro-2-isopropyl-4-pentenoate
α-cyano-3-napthoxy-1-isoquinolinemethyl 5,5-dichloro-3-ethyl-2-isopropyl-4-pentenoate
α-ethynyl-3-(4-chlorophenoxy)-1-isoquinolinemethyl 5,5-dichloro-2,3-diisopropyl-4-pentenoate
α-thiamido-3-(4-ethoxyphenoxy)-1-isoquinolinemethyl 5,5-dibromo-2-isopropyl-4-pentenoate α-cyano-6-phenoxy-2-pyridinemethyl 5,5-difluoro-2-isopropyl-3-methyl-4-pentenoate α-cyano-6-(4-chlorophenoxy)-2-pyridinemethyl 5,5-difluoro-2-isopropyl-3-methyl-4-pentenoate α-cyano-6-(4-[2-propynyloxy]phenoxy)-2-pyridinemethyl 5,5-dichloro-2-isopropyl-3-methyl-4-pentenoate Selected species of the new compounds were evaluated to determine their pesticidal activity against mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°–70° F. and 50–70 percent relative humidity, constituted with test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Bait Test

Larvae of the southern armyworm (*Spodoptera eridania*, (Cram.)), reared on Tendergreen bean plants at a temperature of 80°±5° F. and a relative humidity of 50± percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.), reared according to the specifications of the Chemical Specialities Manufacturing Association (Blue Book, McNair-Dorland Co., N.Y. 1954; pages 243–244, 261) under controlled conditions of 80±° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

Mite Foliage Spray Test

Adults and nymphal stage of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

The results of these tests are set forth in Table I below. In these tests the pesticidal activity of the compounds against aphid, mite, Southern Armyworm, Bean Beetle and house fly was rated as follows:
A=excellent control
B=partial control
C=no control
Dashes indicate no test conducted.

TABLE I

Insecticidal Activity of Phenoxypyridinemethyl Esters of Halo-4-Alkenoic Acids at 500 ppm, A = complete kill, B = some kill, C = no kill

| Example | Structure | Aphid | Mite | SAW | MBB | Fly |
|---|---|---|---|---|---|---|
| V | 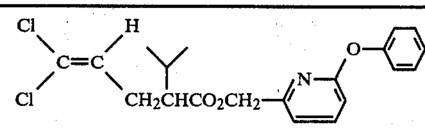 | A | B | A | A | A |
| VI | 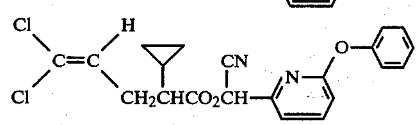 | A | A | A | C | B |
| VII | 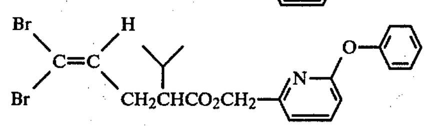 | A | B | A | A | A |
| VIII | 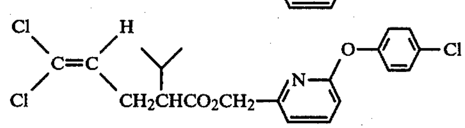 | A | C | B | A | A |
| IX | 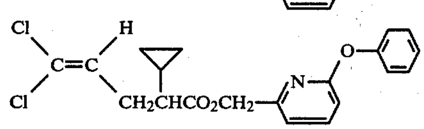 | A | B | C | C | C |
| X | 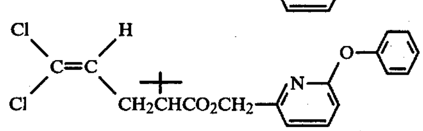 | A | C | B | A | A |
| XI | 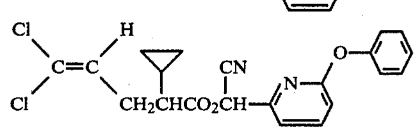 | A | A | A | C | B |
| XII | 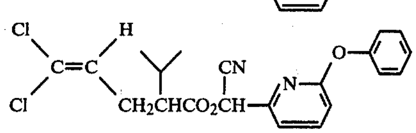 | A | A | A | A | A |
| XIII | 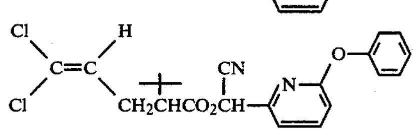 | A | A | A | A | A |

TABLE I-continued

Insecticidal Activity of Phenoxypyridinemethyl Esters of Halo-4-Alkenoic Acids
at 500 ppm, A = complete kill, B = some kill, C = no kill

| Example | Structure | Aphid | Mite | SAW | MBB | Fly |
|---|---|---|---|---|---|---|
| XIV | Cl₂C=CH-CH(CH₃)-CH-CHCO₂CH(CN)-(6-phenoxypyridin-2-yl), isopropyl | A | A | A | A | A |
| XV | Cl₂C=CH-CH(CH₂CH₃)-CH-CHCO₂CH(CN)-(6-phenoxypyridin-2-yl), isopropyl | A | A | B | A | B |
| XVI | Cl₂C=CH-CH(CH₃)-CH(cyclopropyl)-CHCO₂CH(CN)-(6-phenoxypyridin-2-yl) | A | A | A | A | A |
| XVII | Cl₂C=CH-CH(CH₃)-CH(cyclopropyl)-CHCO₂CH₂-(6-phenoxypyridin-2-yl) | A | A | A | A | A |
| XVIII | Cl₂C=CH-CH₂-CH(cyclopropyl)-CHCO₂CH₂-(6-(4-chlorophenoxy)pyridin-2-yl) | A | C | B | C | A |
| XIX | Cl₂C=CH-CH(CH₃)-CH(CH₃)-CHCO₂CH(CN)-(6-phenoxypyridin-2-yl) | A | C | A | A | A |
| XX | Cl₂C=CH-CH(CH₃)-CH(ethyl)-CHCO₂CH(CN)-(6-phenoxypyridin-2-yl) | A | A | A | A | A |
| XXI | Cl₂C=CH-CH(CH₃)-CH(cyclopropyl)-CHCO₂CH(CN)-(6-(4-fluorophenoxy)pyridin-2-yl) | A | A | A | A | A |
| XXII | Cl₂C=CH-CH(CH₃)-CH(isopropyl)-CHCO₂CH(CN)-(6-(4-fluorophenoxy)pyridin-2-yl) | A | A | A | A | A |
| XXIII | Cl₂C=CH-CH(CH₃)-CH(isopropyl)-CHCO₂CH(CN)-(6-(4-chlorophenoxy)pyridin-2-yl) | A | A | A | A | A |

TABLE I-continued

Insecticidal Activity of Phenoxypyridinemethyl Esters
of Halo-4-Alkenoic Acids
at 500 ppm, A = complete kill, B = some kill, C = no kill

| Example | Structure | Aphid | Mite | SAW | MBB | Fly |
|---|---|---|---|---|---|---|
| XXIV | 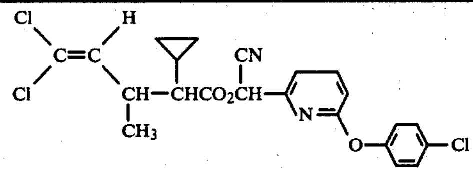 | A | A | A | A | A |

TABLE II

Physical Properties of
Phenoxypyridinemethyl Esters of
Halo-4-Alkenoic Acids

| Example | Molecular Formula | Calculated | | | Found | | |
|---|---|---|---|---|---|---|---|
| | | C | H | N | C | H | N |
| V | $C_{20}H_{21}Cl_2NO_3$ | 60.92 | 5.37 | 3.55 | 61.13 | 5.14 | 3.57 |
| VI | $C_{21}H_{18}Cl_2N_2O_3$ | 60.45 | 4.35 | 6.71 | 60.73 | 4.24 | 6.62 |
| VII | $C_{20}H_{21}Br_2NO_3$ | 49.69 | 4.38 | 2.90 | 49.69 | 4.31 | 2.91 |
| VIII | $C_{20}H_{20}Cl_3NO_3$ | 56.03 | 4.70 | 3.27 | 56.21 | 4.66 | 3.30 |
| IX | $C_{20}H_{19}Cl_2NO_3$ | 61.24 | 4.88 | 3.57 | 61.43 | 4.73 | 3.60 |
| X | $C_{21}H_{23}Cl_2NO_3$ | 61.77 | 5.68 | 3.46 | 61.86 | 5.71 | 3.44 |
| XI | $C_{21}H_{18}Cl_2NO_3$ | 60.45 | 4.35 | 6.71 | 60.73 | 4.24 | 6.62 |
| XII | $C_{21}H_{20}Cl_2NO_3$ | 60.15 | 4.81 | 6.68 | 60.61 | 4.94 | 6.80 |
| XIII | $C_{22}H_{22}Cl_2N_2O_3$ | 60.98 | 5.12 | 6.46 | 60.49 | 5.40 | 6.18 |
| XIV | $C_{22}H_{22}Cl_2N_2O_3$ | 60.98 | 5.12 | 6.46 | 61.33 | 5.17 | 6.45 |
| XV | $C_{23}H_{24}Cl_2N_2O_3$ | 61.75 | 5.41 | 6.26 | 61.97 | 5.44 | 6.07 |
| XVI | $C_{22}H_{20}Cl_2N_2O_3$ | 61.26 | 4.67 | 6.50 | 61.49 | 4.73 | 6.32 |
| XVII | $C_{21}H_{21}Cl_2NO_3$ | 62.08 | 5.21 | 3.45 | 62.40 | 5.27 | 3.47 |
| XVIII | $C_{20}H_{18}Cl_3NO_3$ | 56.29 | 4.25 | 3.28 | 56.80 | 4.28 | 3.14 |
| XIX | $C_{20}H_{18}Cl_2N_2O_3$ | 59.27 | 4.48 | 6.91 | 59.75 | 4.43 | 6.87 |
| XX | $C_{19}H_{20}Cl_2N_2O_3$ | 60.15 | 4.81 | 6.68 | 60.47 | 4.72 | 6.64 |
| XXI | $C_{22}H_{19}Cl_2FN_2O_3$ | 58.81 | 4.26 | 6.24 | 59.30 | 4.26 | 6.14 |
| XXII | $C_{22}H_{21}Cl_2FN_2O_3$ | 58.55 | 4.69 | 6.21 | 58.92 | 4.72 | 6.20 |
| XXIII | $C_{22}H_{21}Cl_3N_2O_3$ | 56.49 | 4.53 | 5.99 | 56.35 | 4.50 | 5.78 |
| XXIV | $C_{22}H_{19}Cl_3N_2O_3$ | 56.13 | 4.11 | 6.01 | 56.87 | 3.99 | 5.51 |

It will be understood that the insect species and other pests employed in the above tests are merely representative of a wide variety of pests that can be controlled by use of the novel compounds of this invention.

The compounds contemplated in this invention may be applied as insecticides, miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents, for example, the condensation products of alkylene oxides with phenol and organic acids, alkyl aryl sulfonates, complex ether alcohols, quaternary ammonium compounds, and the like may be employed for this purpose.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about $\frac{1}{4}$ to 15 pounds of active toxicant per acre.

The pesticides contemplated herein prevent attach by insects, mites upon plants or other material to which the pesticides are applied. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are compatible with other constituents of the spray schedule, and they may be used in the soil, upon the seeds, or the roots of plants without injuring either the seeds or roots of plants. Mixtures of the active compounds may be employed if desired as wll as combinations of the active compounds of this invention with other biologically active compounds.

What is claimed is:

1. A compound of the formula:

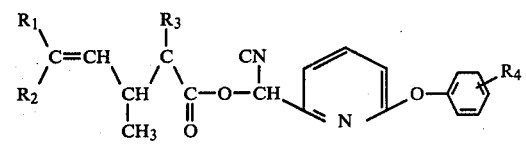

wherein
$R_1$ and $R_2$ are halogen;
$R_3$ may be an alkyl group having from 1 to 5 carbon atoms, branched alkyl, cycloalkyl, alkenyl, branched alkenyl, or cycloalkenyl; and
$R_4$ is hydrogen or halogen.

2. α-cyano-6-phenoxy-2-pyridinemethyl 5,5-dichloro-3-methyl-2-isopropyl-4-pentenoate.

3. α-cyano-6-phenoxy-2-pyridinemethyl 5,5-dichloro-3-methyl-2-cyclopropyl-4-pentenoate.

4. α-cyano-6-phenoxy-2-pyridinemethyl 5,5-dichloro-3-methyl-2-ethyl-4-pentenoate.

5. A pesticide composition comprising an acceptable carrier and an insecticidally or miticidally effective amount of a compound of the formula:

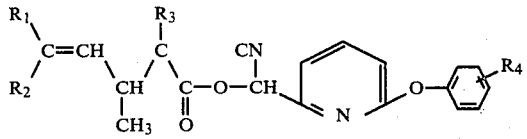

wherein $R_1$ and $R_2$ are halogen;

$R_3$ may be an alkyl group having from 1 to 5 carbon atoms, branched alkyl, cycloalkyl, alkenyl, branched alkenyl, or cycloalkenyl; and $R_4$ is hydrogen or halogen.

6. A pesticide composition as defined in claim 5 wherein said composition is α-cyano-6-phenoxy-2-pyridinemethyl 5,5-dichloro-3-methyl-2-isopropyl-4-pentenoate.

7. A pesticide composition as defined in claim 5 wherein said composition is α-cyano-6-phenoxy-2-pyridinemethyl 5,5-dichloro-3-methyl-2-cyclopropyl-4-pentenoate.

8. A pesticide composition as defined in claim 5 wherein said composition is α-cyano-6-phenoxy-2-pyridinemethyl 5,5-dichloro-3-methyl-2-ethyl-4-pentenoate.

9. A method of controlling insects and mites which comprises subjecting them to a lethal amount of a compound of the formula:

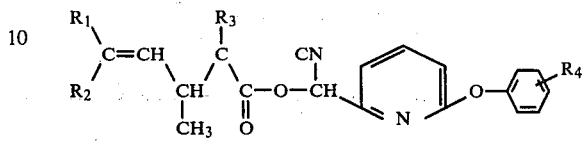

wherein $R_1$ and $R_2$ are halogen;

$R_3$ may be an alkyl group having from 1 to 5 carbon atoms, branched alkyl, cycloalkyl, alkenyl, branched alkenyl, or cycloalkenyl; and $R_4$ is hydrogen or halogen.

10. A method as defined in claim 9 wherein said composition is α-cyano-6-phenoxy-2-pyridinemethyl 5,5-dichloro-3-methyl-2-isopropyl-4-pentenoate.

11. A method as defined in claim 9 wherein said composition is α-cyano-6-phenoxy-2-pyridinemethyl 5,5-dichloro-3-methyl-2-cyclopropyl-4-pentenoate.

12. A method as defined in claim 9 wherein said composition is α-cyano-6-phenoxy-2-pyridinemethyl 5,5-dichloro-3-ethyl-4-pentenoate.

* * * * *

UNITED STATES PATENT AND TRADEMARK OFFICE
CERTIFICATE OF CORRECTION

PATENT NO. : 4,338,326
DATED : July 6, 1982
INVENTOR(S) : P.A. Cain, et al

It is certified that error appears in the above—identified patent and that said Letters Patent is hereby corrected as shown below:

Column 28: line 29; delete "dichloro-3-ethyl-4-pentenoate", insert -- dichloro-3-methyl-2-ethyl-4-pentenoate.--

Signed and Sealed this

Eighth Day of February 1983

[SEAL]

Attest:

GERALD J. MOSSINGHOFF

Attesting Officer    Commissioner of Patents and Trademarks